United States Patent [19]
Elnagar et al.

[11] Patent Number: 5,817,888
[45] Date of Patent: Oct. 6, 1998

[54] BROMINATION PROCESS

[75] Inventors: Hassan Y. Elnagar; Robert L. Davis; Mahmood Sabahi, all of Baton Rouge, La.

[73] Assignee: Albemarle Corporation, Richmond, Va.

[21] Appl. No.: 871,708

[22] Filed: Jun. 9, 1997

[51] Int. Cl.$^6$ ..................................................... C07C 41/24
[52] U.S. Cl. ........................ 568/656; 568/631; 568/737; 568/726; 568/709
[58] Field of Search ..................................... 568/726, 709, 568/663, 656; 564/412

[56] References Cited

U.S. PATENT DOCUMENTS

| | | | |
|---|---|---|---|
| 2,607,802 | 8/1952 | Britton et al. | 260/544 |
| 5,141,652 | 8/1992 | Moore, Jr. et al. | 210/754 |

OTHER PUBLICATIONS

Schulek, E., et al., "Substitutive Halogenation of Aromatic Compounds in Aqueous Solution by Interhaloids—III," *Talantas,* vol. 1, pp. 224–237 (1958), Pergamon Press Ltd., London.

Obeland, C.O., "Aqueous Bromination with Bromine Chloride," *Journal of Chemical Education,* p. 566 (1964).

Mills, J. F., Schneider, J.A., "Bromine Chloride: an Alternative to Bromine," *Ind. Eng. Chem Prod. Res. Develop.,* vol. 12, No. 3, pp. 160–165 (1973).

*Primary Examiner*—Gary Geist
*Assistant Examiner*—Sreeni Padmanabhan
*Attorney, Agent, or Firm*—E. E. Spielman, Jr.

[57] ABSTRACT

A bromination process for organic compounds employs stabilized bromine chloride solutions as the brominating agent. Activated aromatic compounds such as anisole can be selectively monobrominated in the para-position in high purity and yield.

15 Claims, No Drawings

5,817,888

BROMINATION PROCESS

TECHNICAL FIELD

This invention relates generally to the bromination of organic compounds and more specifically to the bromination of organic compounds using a stabilized solution of bromine chloride as the brominating agent. This brominating process can provide regioselectivity in the bromination of activated aromatic compounds.

BACKGROUND

The use of molecular bromine as a brominating agent for both olefinic and aromatic compounds is well known. However, molecular bromine is a corrosive liquid and when used to substitute bromine onto an aromatic ring, HBr is produced as a co-product. The HBr must then be recycled in order to get total bromine utilization. The bromination of aromatic compounds using bromine chloride has been demonstrated. For example, see Britton et al., U.S. Pat. No. 2,607,802. However, bromine chloride is a red-brown liquified gas with a boiling point of about 5° C. Because it is an equilibrium mixture of $Br_2$, $Cl_2$ and BrCl, it also acts as a bromochlorinating agent. Its use as a bromination agent has been reviewed (see Mills et al.,*Ind. Eng. Chem. Prod. Res. Develop.*, 1973, Vol 12, No 3, pp 160). No significant regioselectivity was shown. Aqueous bromine chloride in HCl has been used as an analytical tool for the determination of phenols (see Schuelk et al., *Talanta*, 1958, pp 224). Aqueous bromination using bromine chloride to convert p-nitrophenol to 2,6-dibromo-4-nitrophenol has also been demonstrated (see Obenland, C.O.,*J. Chem. Educ.,*1964, pp 566). It was necessary to prepare BrCl in situ. Stabilized bromine chloride prepared by combining aqueous halide salt solutions or hydrohalic acids with bromine chloride has been used as a biocide for water treatment (see U.S. Pat. No. 5,141,652).

SUMMARY OF INVENTION

We have now found that halide salt stabilized bromine chloride solutions are not only effective, stable, easy to store and handle brominating agents for organic compounds, but which also can provide regioselectivity when used to brominate certain activated aromatic compounds. For example, such compounds can be monobrominated in the para-position with essentially no electrophilic chlorine incorporation. Unlike bromine, total bromine utilization can be achieved without the need to recycle co-product HBr.

In accordance with this invention there is provided a bromination process which comprises reacting an organic compound with a halide salt stabilized bromine chloride solution.

Bromine chloride is typically prepared by reacting equimolar amounts of bromine and chlorine. Other known methods include the reaction of HCl gas with N-bromoacetamide or N-bromosuccinamide in halogenated solvents and the reaction of NaBr with chlorine or Chloramine-T in aqueous solutions.

The stabilized bromine chloride brominating reagent for use in the process of the invention includes a halide salt substituent and, optionally, a hydrohalic acid. The salt substituent comprises a halide anion and an alkali metal, alkaline earth metal, transition metal or quaternary ammonium cation. Preferably, the halide salt is selected from $CaBr_2$, $CaCl_2$, KBr, KCl, LiBr, LiCl, $MgCl_2$, $MgBr_2$, NaCl, NaBr, and the like, including mixtures thereof, with NaCl being a most preferred salt.

The brominating reagent can be formed by mixing the halide salt substituent and, optionally, a hydrohalic acid, (e.g., HCl, HBr, HI and HF) with the bromine chloride by any conventional technique to form an aqueous solution of the ingredients. For example, bromine chloride can be sparged into an aqueous solution of the halide salt as a gas or mixed with the halide salt solution as a liquid. The bromine chloride is preferably used in proportions to provide from about 0.25 to 0.50 mole of bromine chloride per mole of halide salt. The aqueous, stabilized BrCl reagent preferably contains from about 5 to 20 weight %, and more preferably from about 12 to 17 weight %, of the bromine chloride ingredient. An especially preferred reagent is an aqueous $[Na^+(BrCl_2)^-]$ solution prepared by dissolving BrCl in an aqueous NaCl solution. The chloride ion helps to solubilize bromine chloride by complexation in water, i.e., an increase from about 8.5 weight % for BrCl to > 15 weight % as the $[Na^+(BrCl_2)^-]$ complex.

The NaCl stabilized BrCl reagent reacts with olefinic compounds such as, for example, cinnamic acid, cinnamaldehyde, and anethole in a non-specific manner so as to add both chlorine and bromine. They have been found to be very effective brominating agents for at least moderately activated aryl compounds, with monobromination being highly regioselective. In the absence of catalysts there is essentially no (i.e., less than 100 ppm by weight) electrophilic chlorine incorporation.

The brominations can be carried out either in a homogeneous or a two-phase system. For example, in water and/or methanol (homogeneous) or in hydrocarbyl and/or halogenated hydrocarbyl solvents (two-phase). The role of water (from the stabilized BrCl solution) in the bromination of organic molecules in the two-phase system is to scavenge the resulting HCl. Water can also help in promoting a uniform reaction temperature and to partition the heavier-than-water halogenated product from the lighter starting material. Preferably, amounts of solvent of from about 10 to 90 weight % of the total weight of the reaction mixture are used.

The stabilized BrCl brominating reagents are used in equivalent amounts needed to provide the desired degree of bromination of the organic compounds or, if necessary, to complete such bromination, in slight excess. In general, up to about a 20% excess over an equivalent amount of BrCl is sufficient to obtain complete bromination.

The stabilized BrCl reagents are effective without catalysts in the bromination of at least moderately activated aryl compounds to provide selective bromination. For example, bisphenol-A can be converted to tetrabromobisphenol-A in high purity and yield by the process of the invention. Anisole and phenetole are selectively brominated at the para-position with insignificant competition at the ortho-position (regioselectivity). Phenyl ether is also selectively converted to 4-bromophenyl ether, a dibrominated species, with no detectable ortho-bromination. 2,6-Diisopropylaniline is cleanly brominated in 1,2-dichloroethane (EDC) solvent to 4-bromo-2,6-diisopropylaniline in excellent yield without tar formation. 2-Naphthol is cleanly brominated to the corresponding 1-bromo-2-naphthol and 5,5-dimethylhydantoin is brominated in water to provide 1,3-dibromo-5,5dimethylhydantoin. Other aryl compounds which are at least moderately activated by having one or more ring activating groups such as, for example, —OH, —OR, —$NH_2$, —NHR, —$NR_2$, —SR, —SOR, and —OCOR, where R in each case is hydrocarbyl or substituted hydrocarbyl having from about 1 to 30 or more carbons, can likewise be brominated in accordance with the process of the invention under mild conditions. Non-limiting examples of such compounds include phenol, orthoalkylated phenols and disubstituted phenols such as 2,6-dimethyl phenol and 2,6-di-tert-butylphenol, 2-methoxynaphthalene, aniline, orthoalkylated anilines such as o-toluidine, disubstituted anilines, 4-chloroaniline, and the like. Aryl compounds which are only mildly activated, such as toluene, or deactivated, such as benzoic acid, ethyl benzoate, and chlorobenzene, are not brominated in the absence of a catalyst but may undergo bromination in the presence of catalysts such as silica gel, mineral acids, and the like, and such catalyzed bromination processes are considered to be within the scope of this invention.

The reaction temperatures preferably range from about 0° C. up to about 100° C., and more preferably, are at about ambient temperature (i.e., about 18° C. to 25° C.). Reaction rates are usually rapid even below ambient temperature and at atmospheric pressure so that the reactions are, in general, complete in an hour or less.

The invention is further illustrated by, but is not intended to be limited to, the following examples. The stabilized BrCl brominating reagent used in the examples is prepared by dissolving approximately 15 weight % of BrCl in a 3 molar aqueous NaCl solution. The BrCl is prepared by mixing equimolar amounts of bromine and chlorine. The solvents are Baker Analyzed Reagent grade unless otherwise noted. The reactions are monitored by GC using either a 15 m HP-1 column or a J&W 15 m DB-17HT polar column (I.D. 0.32 mm widepore). The structure of all products was determined from NMR, IR, and GC/MS analyses and by comparison with literature data.

The 1H-NMR spectra were obtained at 400 MHZ on a Bruker/GE Omega 400WB or at 300 MHZ on a Bruker/GE spectrometer with deuterochloroform as solvent and TMS as internal standard. The 13C-NMR spectra are obtained at 75.5 MHZ on the Bruker spectrometer QE-300. Mass spectra were obtained on a VG 70SE at 70eV.

Unless otherwise noted, the reactions are carried out in 300-mL round bottom flasks equipped with an addition funnel, magnetic stirrer, stirring bar and a cooling bath when necessary.

EXAMPLE 1

To a solution of phenetole (ethyl phenyl ether, 6.12 g, 50 mmol) in ethylene dichloride (EDC, 100 mL), in a 300-mL round bottom flask cooled in an ice bath, stabilized BrCl brominating reagent (34 mL of 15 weight % solution, about 52 mmol) was added dropwise, with stirring. The ice bath was removed at the end of the addition. The orange reddish solution turned pale yellow. The reaction mixture was quenched with a few drops of saturated sodium sulfite solution, diluted with dichloroethane (100 mL), and washed with water (200 mL). The organic layer was separated and dried ($Na_2SO_4$), and concentrated under reduced pressure to give 10.37 g of an oil (>96% recovered yield). GC area % analysis of the oil showed 0.8% phenetole, 97% 4-bromophenetole, 0.6% 2-bromophenetole, and 1.5% 2,4-dibromophenetole.

EXAMPLE 2

To a solution of anisole (1.08 g, 10 mmol) in EDC (50 mL) cooled in an ice bath, stabilized BrCl brominating reagent was added dropwise, with stirring. The ice bath was removed at the end of the addition. The reaction progress was monitored by GC. A total of 16 mL of the stabilized BrCl solution (about 14 mmol) were added to cause near total conversion of anisole. After standing at room temperature for 0.5 hour, the pale yellow reaction mixture was decolorized when quenched with a few drops of saturated sodium sulfite solution. It was then diluted with methylene chloride (100 mL), washed with water (100 mL), dried ($Na_2SO_4$), and concentrated under reduced pressure. The resulting clear oil (1.61 g, 86% recovered yield) was identified as p-bromoanisole (98% pure). The product was found to contain 2% anisole (GC area %) and only a trace of the ortho isomer was detected.

EXAMPLE 3

To a solution of phenyl ether (3.40 g, 20 mmol) in EDC (50 mL) cooled in a ice bath, stabilized BrCl brominating reagent (38 mL, about 58 mmol) was added dropwise, with stirring. The ice bath was removed at the end of the addition. GC analysis indicated about 80% conversion after 1 hour at room temperature. A longer reaction time did not induce further reaction. An additional 5 mL of brominating reagent was then added (total 43 mL, about 66 mmol) and in less than 1 hour, the starting ether was totally converted to the corresponding dibromide. No evidence of the formation of tri- or tetrabromide products was detected. The reaction mixture was quenched with hydrazine solution, diluted with EDC (100 mL), and washed with water (100 mL). The organic layer was separated, dried ($Na_2SO_4$), and concentrated under reduced pressure to furnish 5.96 g (91% recovered yield) of the dibromide, 4-bromophenyl ether as a highly pure (98% by GC) solid.

EXAMPLE 4

To a solution of 2-naphthol (7.22 g, 50 mmol) in EDC (100 mL) cooled in an ice bath, was added dropwise, stabilized BrCl brominating reagent (30 mL, about 46 mmol). The progress of the reaction was monitored by GC. After standing at room temperature for 20 minutes, approximately 90% conversion was observed. An additional 3 mL of brominating reagent (33 mL total, about 51 mmol) were then added to obtain total conversion after stirring for an additional 30 minutes at room temperature. After quenching with sodium sulfite solution, dilution with EDC (100 mL), and washing with water (200 mL), the organic layer was dried ($Na_2SO_4$) and concentrated to furnish 10.6 g (95% recovered yield) of highly pure (>99% by GC) solid 1-bromo-2-naphthol.

EXAMPLE 5

To a solution of NaOH (0.45 g, 11 mmol) in water (10 mL) cooled in an ice bath, was added 5,5-dimethylhydantoin (0.64 g, 5 mmol). The stabilized BrCl brominating reagent (9 mL, about 14 mmol) was then added dropwise, with stirring to the homogeneous solution. After 5 minutes a slurry was obtained. The dirty white solid was filtered off, washed with water, and dried by filtration to furnish 1.00 g (70% recovered yield) of product which was identified as 1,3-dibromo-5,5-dimethylhydantoin by MNR and IR. There was no evidence of the formation of chlorine containing species.

EXAMPLE 6

To a homogeneous solution of bisphenol-A (BPA, 11.5 g, 50 mmol) in a mixture of EDC (100 mL) and MeOH (20 mL), cooled in an ice bath, stabilized BrCl brominating reagent was added dropwise, with stirring. The BPA is partially soluble in EDC and the product tetrabromobisphenol-A (TBBPA) is totally soluble. The reaction progress was monitored by GC. The brominating reagent was added over two days to test the product stability under extended reaction time. In day 1, a total of 60 mL of reagent was added and the reaction was allowed to stand overnight at room temperature. The next day, an additional 67 mL (total 127 mL, about 196 mmol) of reagent were added to obtain a total conversion to TBBPA. The reaction mixture was quenched with a few drops of sodium sulfite solution. The mixture was diluted with an additional 100 ml, of EDC, washed with water (200 mL), dried ($Na_2SO_4$) and concentrated to furnish 29 g of solid TBBPA. The solid product was dissolved in methanol (100 mL), and the TBBPA was precipitated by the slow addition of distilled water. Filtration furnished 25.65 g (about 94% recovered yield) of highly pure TBBPA (>99 area % by GC). GC/MS analysis of the product detected about 95 ppm by weight chlorine content.

EXAMPLE 7

To a solution of 2,6-dimethyl phenol (2.44 g, 20 mmol) in 1,2-dichloroethane- EDC (50 mL) in a 250-mL round bottom flask, was added the [$Na^+(BrCl_2)^-$] aqueous brominating reagent (23 mL, about 21 mmol) dropwise, with stirring at room temperature. Initially, the orange reddish color of the reagent disappeared quickly. The color from the last mL of reagent persisted for several minutes. The reaction mixture was quenched with a few drops of sodium sulfite solution, and after phase separation, washed with water (100 mL) and dried ($Na_2SO_4$). The organic layer was concentrated under reduced pressure to afford 3.63 g (90% recovered yield) of a highly pure, light brown solid product identified as 4-bromo-2,6-dimethyl phenol.

EXAMPLE 8

To a solution of 2,6-di-tert-butylphenol (2.06 g, 10 mmol) in EDC (50 mL) in a 200-mL round bottom flask, was added the stabilized BrCl brominating reagent (12 mL, about 11 mmol) dropwise, with stirring at room temperature. Initially, the orange reddish color of the reagent disappeared quickly. The color from the last 1 mL persisted for several minutes. The reaction mixture was allowed to stand for 30 minutes before being quenched with a few drops of sodium sulfite solution. After phase separation, it was diluted with EDC (50 mL), washed with water (100 mL) and dried ($Na_2SO_4$). The organic layer was concentrated under reduced pressure to afford a glue-like material. The material was redissolved in ether (10 mL) and after solvent removal, a crystalline solid 4-bromo-2,6-di-tert-butylphenol product (2.63 g, 92% recovered yield) was obtained in high purity (>98% by GC).

What is claimed is:

1. A bromination process which comprises reacting a ring activating group containing aromatic compound with a halide salt stabilized bromine chloride solution such that said aromatic compound is selectively substituted with bromine at the para-position.

2. The process of claim 1 wherein said halide salt is a chloride salt and said stabilized bromine chloride solution comprises a cation selected from the group consisting of alkali metals, alkaline earth metals, transition metals and ammonium and a $BrCl_2^-$ anion.

3. The process of claim 1 wherein said aromatic compound is selected from the group consisting of anisole, phenetole, phenyl ether, orthoalkylated phenols, disubstituted phenols orthoalkylated anilines, disubstituted anilines and 2-phenylphenol.

4. The process of claim 1 wherein said ring activating group is selected from the group consisting of —OH, —OR, —$NH_2$, —NHR, —$NR_2$, —SR, —SOR and OCOR, where R in each instance is hydrocarbyl or substituted hydrocarbyl having from 1 to about 30 carbon atoms.

5. The process of claim 2 wherein said chloride salt is aqueous sodium chloride and said solution comprises aqueous [$Na^+(BrCl_2)^-$].

6. The process of claim 1 wherein said stabilized bromine chloride solution contains from about 0.25 to 0.50 mole of bromine chloride per mole of halide salt.

7. The process of claim 6 wherein the bromine chloride ingredient in said solution constitutes from about 5 to 20 weight percent of said solution.

8. The process of claim 4 wherein said ring activating group is an —OR group.

9. The process of claim 8 wherein said aromatic compound is phenetole and the selective brominated product is 4-bromophenetole.

10. The process of claim 8 wherein said aromatic compound is anisole and the selective brominated product is 4-bromoanisole.

11. The process of claim 8 wherein said aromatic compound is phenyl ether and the selective brominated product is 4-bromophenyl ether.

12. A bromination process which comprises reacting an aromatic compound with a halide salt stabilized bromine chloride solution such that no aromatic ring of said compound is substituted with more than a single bromine atom.

13. The process of claim 12 wherein a single bromine atom is selectively substituted onto said compound.

14. The process of claim 13 wherein said aromatic compound is selected from the group consisting of 2-naphthol and 2-methoxynaphthalene and said aromatic compound is brominated at the 1-position.

15. The process of claim 3 wherein said aromatic compound is 2-phenylphenol and the selective brominated product is 4-bromo-2-phenyl phenol.

* * * * *